United States Patent [19]

Sawaya

[11] Patent Number: 5,516,808
[45] Date of Patent: May 14, 1996

[54] TOPICAL CELLULOSE PHARMACEUTICAL FORMULATION

[76] Inventor: Assad S. Sawaya, 9 Lyn La., Baiting Hollow, N.Y. 11933

[21] Appl. No.: 330,180

[22] Filed: Oct. 27, 1994

[51] Int. Cl.⁶ .......................... A61K 47/38; A61K 31/74; A61K 9/70; A61L 15/16
[52] U.S. Cl. .................. 514/781; 424/78.04; 424/443; 424/445; 424/447; 514/912
[58] Field of Search .................... 424/427, 428, 424/443, 445, 447, 78.04; 514/781, 912

[56] References Cited

U.S. PATENT DOCUMENTS

| | | | |
|---|---|---|---|
| 3,415,929 | 12/1968 | Lachman et al. | 514/157 |
| 3,450,814 | 6/1969 | Bechtold et al. | 514/54 |
| 4,003,991 | 1/1977 | Krohn et al. | 514/10 |
| 4,179,497 | 12/1979 | Cohen et al. | 424/428 |
| 4,271,143 | 6/1981 | Schoenwald et al. | 514/9 |
| 4,343,787 | 8/1982 | Katz et al. | 424/428 |
| 4,349,563 | 9/1982 | Gilbert et al. | 514/423 |
| 4,474,751 | 10/1984 | Haslam et al. | 514/11 |
| 4,511,563 | 4/1985 | Schmolka | 514/162 |
| 4,551,456 | 11/1985 | Katz et al. | 514/254 |
| 4,678,855 | 7/1987 | Shepard et al. | 564/85 |
| 4,767,619 | 8/1988 | Murray | 424/445 |
| 4,861,755 | 8/1989 | Breipohl et al. | 514/11 |
| 4,861,760 | 8/1989 | Mazuel et al. | 514/54 |
| 4,883,660 | 11/1989 | Blackman et al. | 514/255 |
| 5,013,545 | 5/1991 | Blackman et al. | 514/716 |
| 5,137,728 | 8/1992 | Bawa et al. | 424/427 |
| 5,141,928 | 8/1992 | Goldman | 514/54 |
| 5,164,188 | 11/1992 | Wong | 424/428 |
| 5,229,128 | 7/1993 | Haddad et al. | 424/427 |
| 5,252,318 | 10/1993 | Joshi et al. | 424/78.04 |
| 5,259,998 | 11/1993 | Reich | 264/1.1 |
| 5,292,517 | 3/1994 | Chang | 424/426 |
| 5,300,295 | 4/1994 | Viegas et al. | 424/427 |
| 5,318,780 | 6/1994 | Viegas et al. | 424/427 |

*Primary Examiner*—Carlos Azpuru
*Attorney, Agent, or Firm*—Darby & Darby

[57] ABSTRACT

The invention relates to an improved topical formulation, which is substantially free of an oil phase, and contains at least one antibiotic, purified water, and a gelling agent in an amount sufficient to form an aqueous gel.

24 Claims, No Drawings

[5,516,808]

TOPICAL CELLULOSE PHARMACEUTICAL FORMULATION

FIELD OF THE INVENTION

The present invention is in the field of topical pharmaceutical formulations.

BACKGROUND OF THE INVENTION

Polymyxin is a generic term for a group of closely related antibiotic substances. Polymyxin B is the least toxic of these and is currently available for clinical use. Polymyxin B Sulfate is readily soluble in water. Aqueous solutions are quite stable at physiological pH. A 2% aqueous solution has a pH of about 5.7. The activity of Polymyxin B is restricted to gram-negative bacteria. A concentration of 0.1 to 0.25% in aqueous solution is said to be non-irritating and effective.

Neomycin is a complex of three compounds, Neomycins A, B & C. Commercial preparations are made with Neomycin B, which is a water soluble, thermostable substance. The sulfate complex is stable in the dry state, or in solution, at room temperature. It is a broad spectrum antibiotic, commonly marketed in dermatological and ophthalmic ointments, or as a sterile powder for dilution with saline solution for topical application or parenteral injection.

Several topical antibiotic formulations are known that employ Polymyxin B Sulfate in a suspension in combination with Neomycin Sulfate. Some such formulations include additional active ingredients, such a Lidocaine Hydrochloride and/or Zinc Bacitracin. These products are available in an oil base, such as in petrolatum, mineral oil, emulsifying wax, or a combination of those substances. Some examples of commercially sold formulations include the following:

Neosporin™ ointment: made of Polymyxin B Sulfate, Neomycin, Zinc Bacitracin, and Lidocaine, in emulsifying wax, mineral oil, purified water, and white petrolatum.

Campho-Phenique™ Triple Antibiotic Ointment Plus Pain Reliever: containing Zinc Bacitracin, Neomycin Sulfate, Polymyxin B Sulfate, and Lidocaine in a white petrolatum base.

Mycatracin™ Triple Antibiotic First Aid Ointment: Bacitracin, Neomycin Sulfate, Polymyxin B Sulfate in a microcrystalline wax, mineral oil and white petrolatum base. Micatrin™ Plus Pain Reliever also contains Lidocaine.

The base in these formulations, however, holds the actives in an oil phase, and does not allow quick, or sufficient, release to areas to be treated. Furthermore, application of these formulations in the oil phase creates the possibility of stained clothing.

Polymyxin B Sulfate has been used in combination with Neomycin Sulfate in specialized applications as well, including ophthalmic ointments (e.g., petrolatum based), otic sterile solutions, and ophthalmic sterile solutions. In a conventional ophthalmic ointment, antibiotics are suspended in petrolatum and mineral oil. Upon application of a dose to the eye, a portion is expelled, and spreading of the dose inhibited, because oily fluids are rejected. Furthermore, release of the active ingredient is delayed for the time required to exchange water from aqueous eye fluid. As a result, an inexact amount of the active ingredient reaches the site being treated. Solutions suffer similar deficiencies because they run out of the eye upon administration. Thus, with an ophthalmic ointment or solution, only a low, and imprecise amount of the antibiotic reaches the use point.

SUMMARY OF THE INVENTION

The present invention, in one embodiment, is an improved topical first aid antibiotic gel formulation adapted for non-ophthalmic use. The formula comprises at least one antibiotic, purified water, and an amount of gelling agent effective to form an aqueous gel. The gel has a viscosity of from 25,000 to 300,000 centipoise. The formulation is substantially free of an oil phase. The antibiotic is solubilized in the formulation. Also included in the invention is a method of administering the first aid formulation to an area of an individual's skin in need of first aid, and allowing an occlusion to form upon evaporation of the purified water. In addition, the invention includes a dispensing device adapted for non-ophthalmic topical use, containing the first aid formulation.

In another embodiment, the invention relates to a sterile medication adapted for ophthalmic use containing at least one antibiotic suitable for ophthalmic administration, purified water, and an amount of gelling agent effective to form an aqueous gel. The gel has a viscosity of from 25,000 to 300,000 centipoise. The formulation is substantially free of an oil phase. The antibiotic is solubilized in the formulation. Also included in the invention is a method that involves administering the sterile medication to the eye of an individual.

In a further embodiment, the invention relates to a topical formulation comprising at least one medically active substance, purified water, and an amount of a cellulose based gelling agent effective to form an aqueous gel. The gel has a viscosity of from 25,000 to 300,000 centipoise. The formulation is substantially free of an oil phase. The medically active substance is solubilized in the formulation.

DETAILED DESCRIPTION OF THE INVENTION

The topical first aid formulation of this invention improves over existing oil based topical formulations incorporating antibiotics. The term "oil based" is used here to refer to formulations containing an oil phase. The present topical first aid formulation acts faster to better prevent infection. It also delivers a more certain amount of drug. In addition, it does not present the handling difficulties of oil based formulations. The topical first aid gel is also advantageous in forming an occlusion, following application, that protects the area being treated.

The ophthalmic antibiotic medication of the invention in particular improves over existing oil based formulations, and solutions. Upon administration, aqueous eye fluids mix with the antibiotic in the formulation gel, resulting in the antibiotic's immediate release. Also, a predetermined dose reaches the site being treated. Furthermore, a much higher percentage of a properly administered dose is maintained in the eye than with a conventional ophthalmic antibiotic ointment or solution. Therefore, a smaller dose is required.

In a preferred embodiment, the formulation contains Polymyxin B Sulfate, and Neomycin Sulfate. Most preferably it contains both. These antibiotics have been found to exhibit unexpectedly high release rates in the formulation.

The formulations of the invention can be placed in any desired dispensing devices, including tubes, jars, spray pumps or aerosol pumps. The non-ophthalmic formulation can be placed in any dispensing device adapted for non-ophthalmic use. The ophthalmic medication can be in the form of an ophthalmic delivery system. An example of such a system is a sterile ophthalmic tube, such as a conventional 3.5 g tube, having an ophthalmic tip and containing the ophthalmic formulation.

Conventional gelling agents can be used in the antibiotic containing embodiments of this invention. Cellulose and its derivatives are preferred. Most preferred is hydroxypropyl methyl cellulose (such as Methocel™ E4M). Other gelling agents include methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum. Cellulose based gelling agents, particularly hydroxymethylcellulose and hydroxypropyl methyl cellulose, are advantageous over, for example, cross-linked acrylic polymers. Carbopol™, a cross-linked acrylic polymer, has been used to form an aqueous gel containing pilocarpine hydrochloride for ophthalmic use. The cellulose based gelling agents, however, are less likely to cause adverse reactions.

The formulations of the invention are substantially viscous enough to form a firm gel. The viscosity preferably is in the range of 25,000–300,000 cps (centipoise), most preferably 75,000–200,000 cps, based on Brookfield (LV) analysis.

In the topical gel of the invention adapted for first aid non-ophthalmic use, an effective amount of the gelling agent forms an occlusion upon evaporation of the purified water. For example, a suitable amount of cellulose or cellulose derivative for this purpose is from about 1 wt. %–5 wt. %. Suitable amounts of other gelling agents can be determined by one skilled in the art.

In the aqueous gel for ophthalmic use, the amount of cellulose based gelling agent is preferably from about 1 wt. %–5 wt. %, most preferably from about 2.5 wt. %– 3.5 wt. %.

The formulation may contain additional pharmaceutically inactive substances. For example, it may contain one or more solubilizing agents, such as polysorbate 20, polysorbate 40, polysorbate 60 or polysorbate 80. The topical or ophthalmic agent may also contain a dispersant, such as lecithin or glycerine. Collagen can also be added, particularly in ophthalmic gels. Other additives include cyclodextrins, in particular alpha, beta, and gamma cyclodextrins. Also, vitamin E, particularly in a solubilized form, or other antioxidants, including butylate hydroxyanisole (BHA) and butylate hydroxytoluene (BHT), may be added. Some additional examples of inactives follow, including in some cases typical amounts for an ophthalmic formulation: benzalkonium chloride (0.01%), boric acid (0.1–0.1%), sodium carbonate (1.0%), potassium chloride (0.2%), propylene glycol, polyoxyethylene, polyoxypropylene, cetyl alcohol, glyceryl monostereate, polyoxyl40 stearate, glycerin (1%), polyvinyl alcohol (1.4%), poloxamer 188, sodium citrate, sodium thiosulfate (0.3%), sodium bisulfite, dextran 70 (0.1%), tyloxagol (0.25%), acetic acid, polyethylene glycol 300, povidone, gelatin A (0.01%), dextrose, magnesium chloride, alginic acid, and sodium borate. The optimal amount of inactive ingredient employed in the formulation can be conventionally determined based on the particular active pharmaceutical, and the intended use, e.g. ophthalmic use, first aid to a wound, etc.

Preferred amounts of antibiotics are Polymyxin B Sulfate (5,000–10,000 units/gin) Neomycin Sulfate (1.75–3.5 mg/gm). Other antibiotics, in their preferred amounts, include Gramicidin (0.025 mg/gm), Zinc Bacitracin (400–500 units/gm), Gentamicin (0.3%); Chloramphenicol (0.5%), Tobramycin (0.3%), Erythromycin, (5 mg/gm), and Tetracycline HCl (1%).

The formulation may include asteroid. Examples of such steroids, and preferred amounts, include Hydrocortisone (1%), Prednisone (0.1%), Fluorometholone acetate (0.1%), Dexamethasone Sodium Phosphate (0.05%), Dexamethasone (0.1%), Suprofen (1%), Fluorometholone (0.1%–0.25%), and Medrysone (1.0%).

Commercially available pharmaceutically active drugs for use in the aqueous gel of the invention, include, without limitation (the preferred concentrations being indicated in parentheses following each ingredient), Proparacaine HCl (0.5%), Betaxolol HCl (0.5%, Cyclopentolate HCl (0.5%–2%), Phenylephrine HCl (1%–10%), Epinephrine (1.0%–2.0%), Apraclonidine HCl (1%), Atropine sulfate (0.5%–1.0%), Carbachol (0.75%–3.0%), Pilocarpine HCl (0.25%, 0.5%, 1%, 2%, 3%, 4%, 5%, 6%, 8%, and 10%), Sulfacetamide sodium (10%), Homatropine Hydrobromide (2.0%– 5.0%), Scopolamine Hydrobromide (0.25%), Tropicamide (0.5%–1.0%), Naphazoline HCl (0.1%), Tetrahydrozoline Hydrochloride (0.05%), Oxymetazoline Hydrochloride (0.025%), Ketorolac Tromethamine (0.5%), Levobunolol HCl (0.25%–0.5%), Idoxuridine (0.1%), Trimethoprim (1 mg/gm), Dipivefrin HCl (0.1%), Metipranolol (0.3%), Trifluridine (1%), Diclofenac Sodium (0.1%), Zinc Isoflurophate (0.25%), Demecarium Bromide (0.125%–0.25%), Timolo Maleate (0.25%–0.5%), Carteolol HCl (10 mg/gm), and Vidarabine (3%).

In a "triple antibiotic" form of the invention, i.e., including at least Polymyxin B, Neomycin Sulfate and Zinc Bacitracin, one or more agents are added to stabilize the Zinc Bacitracin. Lidocaine HCl is preferred for this purpose. The Lidocaine HCl is preferably present in about 1–4 wt. % of the amount of Zinc Bacitracin, most preferably 400 to 500 units per gram. Dispersing Zinc Bacitracin in methyl cellulose or another cellulose derivative will further enhance the stability of the Zinc Bacitracin. Other agents which can be used to stabilize Zinc Bacitracin include Acetamide, Acetanilide, Acetoacetamide, Acetoacetanilide, Glycine, Methylacetanilide, 4-Aminoacetanilide, Glycinamide HCl, 4-Fluoroacetanilide, Benzamide, Benzamide HCl, N,N-diphenylacetamide, 4-Nitroacetanilide, Thioacetanilide, Thioacetamide, Glycine Hydrochloride, Glycyl Glycine, Methoxy Benzamide, N-Methylacetamide, N-Ethylacetamide, 2-Chloroacetamide, 2-Chloroacetanilide, 3-Chloroacetanilide, 4-Chloroacetanilide, 2-Bromoacetamide, 4-Bromoacetanilide, Formamide, 2-Fluoroacetanilide and 3-Fluoroacetanilide.

Following are some examples of combinations of Polymyxin B Sulfate and additional actives that can be used in a topical formulation of the invention.

| | | |
|---|---|---|
| A) | Polymyxin B Sulfate | 5,000–10,000 units |
| | Neomycin Sulfate | 3.5 mg (as base) |
| | Lidocaine Hydrochloride | 40 mg (as base) |
| B) | Polymyxin B Sulfate | 5,000–10,000 units |
| | Neomycin Sulfate | 3.5 mg (as base) |
| | Zinc Bacitracin | 400–500 units |
| | Lidocaine Hydrochloride | 40 mg (as base) |
| C) | Polymyxin B Sulfate | 5,000–10,000 units |
| | Zinc Bacitracin | 400–500 units |
| | Lidocaine Hydrochloride | 40 mg (as base) |

Benzocaine (5%–20%) or Benzocaine Hydrochloride can be substituted for Lidocaine.

Examples of antibiotic combinations in the ophthalmic delivery system of the invention are shown below.

| | | |
|---|---|---|
| A) | Polymyxin B Sulfate | 10,000 units |
| | Neomycin Sulfate | 3.5 mg (as base) |
| | Zinc Bacitracin | 400 units |
| B) | Polymyxin B Sulfate | 10,000 units |
| | Zinc Bacitracin | 500 units |
| C) | Polymyxin B Sulfate | 10,000 units |
| | Neomycin Sulfate | 1.75 mg (as base) |
| | Gramicidin | 0.025 mg |
| D) | Polymyxin B Sulfate | 10,000 units |
| | Neomycin Sulfate | 3.5 mg (as base) |
| | Zinc Bacitracin | 400 units |
| | Hydrocortisone | 1% |
| E) | Polymyxin B Sulfate | 10,000 units |
| | Neomycin Sulfate | 3.5 mg (as base) |
| | Hydrocortisone | 1% |
| F) | Polymyxin B Sulfate | 10,000 units |
| | Neomycin Sulfate | 3.5 mg |
| | Dexamethasone | 0.1% |
| G) | Polymyxin B Sulfate | 10,000 units |
| | Neomycin Sulfate | 3.5 mg |
| | Prednisolone Acetate | 0.5% |

The invention is illustrated by the following examples.

Example 1

A first aid antibiotic topical gel was made containing the following actives: Polymyxin B Sulfate (5,000–10,000 units per grams); Neomycin Sulfate (3.5 milligrams base/gram); Lidocaine Hydrochloride (40 milligrams base/gram). The following procedure was used.

25.80 kilograms of purified water was transferred into a 75 gallon capacity stainless steel kettle, equipped with a mixing device. Agitation was performed at 10–20 RPMS (22.5–45 Hz). pH was checked and adjusted between 3.5 and 4.2 by adding 10% v/v HCl. Mixing was done thoroughly after adding each aliquot and then checking the pH. Agitation was then adjusted to 30–40 RPMS (67–90 Hz).

The following were added, making sure each was dissolved in solution before adding the next:

0.480 kg Neomycin Sulfate (Micronized USP);

0.1603 kg Polymyxin B Sulfate (Micronized USP);

4.0682 kg Lidocaine HCl USP (86.54% as base);

1600.0 grams Tween™ 20;

320.0 grams Vitamin E.

6,000 grams of propylene glycol was transferred into a 5 gallon capacity stainless steel kettle equipped with a mixing device. While mixing, the temperature was raised to 80°–90° C. (The type and speed of the mixing device are not believed critical.) The following ingredients were added in the order given, make sure each was completely dissolved before adding the next: 80 grams BHT; 80 grams BHA.

The contents of the kettle were then transferred into the mixture containing the Neomycin Sulfate, Polymyxin B Sulfate, Lidocaine Hydrochloride etc.

39.4 kilograms of purified water was transferred into a 20 gallon capacity stainless steel kettle equipped with a mixing device. While mixing, the temperature of the water was brought to 80°–90° C. and 2.4 kilograms Methocel™ 4M (hydroxypropyl methyl cellulose)added while mixing. The Methocel™ 4M was disbursed evenly, eliminating any lumps. The contents of the kettle were brought to 45°–55° C. and then added to the mixture containing the Neomycin Sulfate etc. Slow mixing was done for 20–30 minutes to avoid entrapment of air. Temperature was lowered to 30° C. and mixing stopped. Other formulations were made using different antioxidants and preservatives, including sodium edetate and benzalkonium chloride.

Example 2

The potency of antibiotic preparations can be demonstrated by measuring their inhibitory effects on selected micro-organisms under controlled conditions. Procedures for doing this are found in The United States Pharmacopeia (UNITED STATED PHARMACOPEIAL CONVENTION, INC., THE UNITED STATES PHARMACOPEIA/THE NATIONAL FORMULARY (1995) p. 1690). The same methods may be used to compare, quantitatively, the ability of different formulation bases to release antibiotics to areas they are applied to. The preparation which diffuses the most antibiotic is considered to be the most effective. This procedure was used to compare antibiotics in the aqueous gel formulation of the invention with conventional antibiotic ointment formulations.

Procedure

Assay plates were prepared containing two layer of media (a base layer and a seed layer) designed to promote the rapid growth of selected micro-organisms. The media were liquified, inoculated with a purified culture, poured into petridishes and allowed to solidify. A stainless steel cylinder was then placed in the middle of the plate, with one of its open faces flush against the medium. The cylinders were filled with the product to be tested and placed in an incubator. After 24 hours the plates were removed from the incubator and observed.

On each plate a circular zone surrounding the cylinder was formed where no microbial growth was observed. This zone is formed as the antibiotic diffuses out of the formulation base in the cylinder and into the inoculated media. The diffusing antibiotic spreads outward, inhibiting the growth of micro-organisms. The greater the amount of antibiotic released from the preparation, the larger the zone formed. Diffusion effectiveness may be observed by comparing zone diameter measurements.

The diffusion effectiveness of three different antibiotics (Neomycin Sulfate, Polymyxin B Sulfate and Bacitracin Zinc) was evaluated for both the aqueous gel formulation of this invention and a conventional triple antibiotic ointment. Each formulation contained the same potency of antibiotic.

Results

Results were as follows:

| | | | Zone Diameter | |
|---|---|---|---|---|
| Antibiotic | Base Form | Potency | Test 1 | Test 2 |
| Zinc | Ointment | 400 IU/gm | 19.2 mm | 22.2 mm |
| Bacitracin | Gel | " | 29.3 mm | 28.0 mm |
| Polymyxin B | Ointment | 10,000 IU/gm | 15.4 mm | 18.6 mm |
| Sulfate | Gel | " | 26.4 mm | 26.8 mm |
| Neomycin | Ointment | 3.5 mg base/gm | 18.2 mm | 19.8 mm |
| Sulfate | Gel | " | 25.2 mm | 28.6 mm |

Observations and Conclusions

In all cases, the zone diameter of the antibiotic in the aqueous gel base was significantly greater than that of the corresponding ointment base. The relative amount of antibiotic delivered into the medium from each formulation type was determined by a comparison of the areas of the individual zones. This calculation showed that the gel base Zinc Bacitracin formula delivered at least 59% more antibiotic than the traditional ointment, that Polymyxin B Sulfate delivered at least more, and Neomycin Sulfate delivered at least 92% more.

Example 3

Release rates of antibiotic from the gel formulation of the invention were compared with those of a conventional oil based formulation. The procedure of Example 2 was followed. The units/gram released were calculated from zone size.

Following are results obtained for three microorganisms tested.

A. *Bordetella Bronchiseptica*

Release of Polymyxin B Sulfate from the base formulation was measured in the amounts shown.

| Run | Triple Ointment Units/Gram | Triple Gel Units/Gram |
| --- | --- | --- |
| 1 | 11.5 | 332.1 |
| 2 | 4.7 | 496.6 |
| 3 | 10.1 | 987.0 |
| Average | 8.76 | 602.2 |
| 602.2/8.76 = 68.74 times greater release rate | | |

B. *Micrococcus Luteus*

Release of Zinc Bacitracin from the base formulation was measured in the amounts shown.

| Run | Triple Ointment Units/Gram | Triple Gel Units/Gram |
| --- | --- | --- |
| 1 | 0.4 | 22.9 |
| Average | 0.4 | 22.9 |
| 22.9/0.4 = 57.25 times greater release rate | | |

C. *Staphylococcus Epidermis*

Release of Neomycin from the base formulation was measured in the amounts shown.

| Run | Triple Ointment mg/gm | Triple Gel mg/gm |
| --- | --- | --- |
| 1 | 0.0013 | 0.015 |
| 2 | 0.0037 | 0.019 |
| Average | 0.0025 | 0.016 |
| 0.01675 = 6.7 times greater release rate | | |

These results show a higher release rate for the antibiotics in the aqueous gel formulation of the invention than for a corresponding ointment. The release rates for Polymyxin B Sulfate and Zinc Bacitracin were much higher than expected, i.e., 69 and 57 times the ointment release rate, respectively.

Example 4

An aqueous gel of 0.025% Oxymetazoline HCl was prepared containing Parts A and B as follows:

| Part A | |
| --- | --- |
| Purified Water | 200 grams |
| Boric Acid | 9.6 grams |
| Sodium Borate | 0.13 grams |
| Edetate Disodium | 1.0 grams |
| Benzalkonium Chloride | 0.1 grams |
| Oxymetazoline HCl | 0.26 grams |
| Sodium Chloride | 4.0 grams |
| Part B | |
| Purified Water | 750 grams |
| Hydroxypropyl Methyl Cellulose | 35 grams |

Part A: All ingredients in Part A were mixed and dissolved, in the order listed, until a clear solution was obtained. The solution was then sterilized by membrane filtration (0.2 microns).
Part B: Purified water was heated to 90° C. Hydroxypropyl Methyl cellulose was added and mixed until it was uniformly dispersed. While mixing in a pressure vessel, the mixture was sterilized at 121° C. for 30–45 minutes.

The temperature was brought down to 50°–55° C. Part A was then aseptically added. Mixing was continued, and the temperature lowered to 25°–30° C. A gel resulted that was used to aseptically fill pre-sterilized 3.5 gram ophthalmic tubes.

Example 5

The ophthalmic oxymetazoline HCl preparation made in Example 4 was administered as follows. To avoid contamination, the tip of the container was not touched to any surface and the cap replaced after using. The lower lid of the eye administered to was pulled down and a small amount of gel applied (approximately one fourth inch (¼")) to the inside of the eyelid. The weight of the ¼ inch ribbon was about 20 mg.

On two separate days, 1 week apart, the gel was administered as above. The first day, the gel was administered to the left eye, the second to the right eye. In both cases, the gel was not expelled. There was a slight feeling of pressure around the lid area where the gel was applied. Within minutes, the treated eye turned white as compared with the untreated eye. After application of the gel, slight pressure discomfort seemed to lessen. After 30–45 minutes, no pressure was felt. The difference in color between the eyes remained for 2–4 hours.

Example 6

Aqueous gel preparations containing 3.5% methylcellulose and purified water were prepared. These formulations contained the following actives per gram:

| Polymyxin B Sulfate | 10,000 units |
| --- | --- |
| Neomycin Sulfate | 3.5 mg. as base |
| Lidocaine HCl | 40 mg. as base |

The gel had a viscosity range of 175,000–225,000 cps. It was applied to skin (0.5–1.0 gram) and gently spread over a 1.0 inch diameter. A moist clear film developed over the area covered by the gel. After 1 hour, the film was clear, and appeared to be continuous and occlusive. The film remained clear and continuous for at least five hours after application. After six hours, the film started to look opaque, and the edges started to peel off. A continuous piece could be removed by its raised edges, indicating that the film was still occlusive. This film appears to provide additional protection against infection of minor cuts, burns and abrasions.

I claim:

1. A topical first aid antibiotic gel formulation adapted for non-ophthalmic use comprising at least one antibiotic in a therapeutically effective amount for those in need thereof, purified water, and an amount of a gelling agent effective to form said gel, said formulation being substantially free of an oil phase, said gel having a viscosity of from 75,000–300,000 cps at a temperature from 25° to 30° C., and said antibiotic being solubilized in said formulation, wherein said gelling agent consists essentially of cellulose or a cellulose derivative in an amount of from 1 to 5 wt. %, and wherein said cellulose derivative is selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum.

2. An antibiotic formulation according to claim 1 having a viscosity of from 75,000–200,000 cps.

3. An antibiotic formulation according to claim 1 comprising Polymyxin B Sulfate and Neomycin Sulfate.

4. An antibiotic formulation according to claim 1 comprising Polymyxin B Sulfate, Neomycin Sulfate, and Zinc Bacitracin.

5. An antibiotic formulation according to claim 1 wherein said gelling agent is selected from the group consisting of hydroxy methyl cellulose and hydroxypropyl methyl cellulose.

6. An antibiotic formulation according to claim 1 wherein said gelling agent is selected from the group consisting of methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum.

7. An antibiotic formulation according to claim 1 further comprising asteroid solubilized in said aqueous gel.

8. An antibiotic formulation according to claim 7 wherein said steroid is selected from the group consisting of Hydrocortisone, Prednisone, Flouromethoione acetate, P-examethasone Sodium Phosphate, Dexamethasone, Suprofen, Flouromethoione, and Medrysone.

9. A sterile medication adapted for ophthalmic use comprising an aqueous gel formulation comprising at least one antibiotic suitable for ophthalmic administration in a therapeutically effective amount for those in need thereof, purified water, and an amount of a gelling agent effective to form said gel, said gel having a viscosity of from 75,000 to 300,000 cps at a temperature from 25° to 30° C., said formulation being substantially free of an oil phase, said antibiotic being solubilized in said formulation, wherein said gelling agent consists essentially of cellulose or a cellulose derivative in an amount of from 1 to 5 wt. % and wherein said cellulose derivative is selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum.

10. A medication according to claim 9 wherein said gel has a viscosity of from 75,000 to 200,000 cps.

11. A medication according to claim 1 comprising Polymyxin B Sulfate and Neomycin Sulfate.

12. A medication according to claim 1 comprising Polymyxin B Sulfate, Neomycin Sulfate, and Zinc Bacitracin.

13. An ophthalmic delivery system containing the medication of claim 9.

14. An ophthalmic delivery system of claim 13 comprising a sterile ophthalmic tube having an ophthalmic tip and containing said aqueous gel.

15. A medication according to claim 9 wherein said gelling agent is selected from the group consisting of hydroxypropyl methyl cellulose and hydroxy methyl cellulose.

16. A medication according to claim 9 wherein said gelling agent is selected front the group consisting of methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum.

17. A method comprising administering the sterile medication of claim 9 to the eye of an individual.

18. A topical gel formulation comprising at least one pharmaceutically active substance in a therapeutically effective amount for those in need thereof, purified water, and an amount of a cellulose based gelling agent effective to form an aqueous gel, said formulation being substantially free of an oil phase, said gel having a viscosity of from 75,000 to 300,000 cps at a temperature of from 25° to 30° C., said pharmaceutically active substance being solubilized in said formulation, wherein said gelling agent consists essentially of cellulose or a cellulose derivative in an amount of from 1 to 5 wt. %, and wherein said cellulose derivative is selected from the group consisting of hydroxypropyl methyl cellulose, hydroxymethyl cellulose, methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum.

19. A formulation according to claim 18 wherein said gel has a viscosity of from 75,000 to 200,000 cps.

20. A formulation according to claim 18 adapted for ophthalmic use.

21. A formulation according to claim 18 wherein said gelling agent is selected from the group consisting of hydroxypropyl methyl cellulose and hydroxy methyl cellulose.

22. A formulation according to claim 21 wherein said medically active substance is Polymyxin B Sulfate.

23. A method comprising administering the formulation of claim 18 to an area on an individual's skin in need of first aid.

24. A method comprising administering the formulation of claim 18 to the eye of an individual.

* * * * *